(12) United States Patent
Corradi et al.

(10) Patent No.: US 10,822,291 B2
(45) Date of Patent: *Nov. 3, 2020

(54) PROCESSES AND APPARATUSES FOR NAPHTHENE RECYCLE IN THE PRODUCTION OF AROMATIC PRODUCTS

(71) Applicant: UOP LLC, Des Plaines, IL (US)

(72) Inventors: Jason T. Corradi, Arlington Heights, IL (US); Patrick C. Whitchurch, Sleepy Hollow, IL (US); Abhishek M. Pednekar, Schaumburg, IL (US); Leonid Bresler, Northbrook, IL (US); Anton N. Mlinar, Vernon Hills, IL (US)

(73) Assignee: UOP LLC, Des Plaines, IL (US)

( * ) Notice: Subject to any disclaimer, the term of this patent is extended or adjusted under 35 U.S.C. 154(b) by 90 days.

This patent is subject to a terminal disclaimer.

(21) Appl. No.: 16/039,139

(22) Filed: Jul. 18, 2018

(65) Prior Publication Data
US 2018/0319724 A1 Nov. 8, 2018

Related U.S. Application Data

(63) Continuation of application No. PCT/US2017/023393, filed on Mar. 21, 2017.
(Continued)

(51) Int. Cl.
*C07C 7/08* (2006.01)
*C07C 5/27* (2006.01)
(Continued)

(52) U.S. Cl.
CPC .................. *C07C 7/08* (2013.01); *B01D 3/40* (2013.01); *C07C 5/08* (2013.01); *C07C 5/27* (2013.01);
(Continued)

(58) Field of Classification Search
CPC ......... C07C 7/08; C07C 15/08; C07C 15/073; C07C 15/06; C07C 2/66; C07C 2/76;
(Continued)

(56) References Cited

U.S. PATENT DOCUMENTS 3,538,173 A * 11/1970 Berger .................. C07C 5/2791
585/482
3,562,344 A * 2/1971 Hengstebeck et al. .....................
C07C 15/08
585/477

(Continued)

FOREIGN PATENT DOCUMENTS

FR 2922547 A1 4/2009

OTHER PUBLICATIONS

Written Opinion from corresponding PCT Application No. PCT/US217/023393, dated Jun. 13, 2017.
(Continued)

*Primary Examiner* — Youngsul Jeong

(57) ABSTRACT

Processes and apparatuses for producing a $C_8$ aromatic isomer product are provided. The processes comprise introducing a raffinate product stream comprising $C_8$ aromatic isomers to an isomerization unit to provide an isomerized stream. The isomerized stream is separated to provide a first stream comprising $C_8$ naphthenes and $C_7$ aromatic hydrocarbons and a second stream comprising $C_8$ aromatic isomers. The first stream is passed to an extractive distillation column to provide a recycle feedstream comprising the $C_8$ naphthenes and an extract stream comprising the $C_7$ aromatic hydrocarbons. The recycle feedstream is passed to the isomerization unit.

14 Claims, 2 Drawing Sheets

Related U.S. Application Data

(60) Provisional application No. 62/316,446, filed on Mar. 31, 2016.

(51) Int. Cl.
*C07C 15/08* (2006.01)
*C07C 15/073* (2006.01)
*C07C 5/08* (2006.01)
*B01D 3/40* (2006.01)
*C07C 15/06* (2006.01)

(52) U.S. Cl.
CPC .............. *C07C 5/277* (2013.01); *C07C 15/06* (2013.01); *C07C 15/073* (2013.01); *C07C 15/08* (2013.01); *B01D 2257/7027* (2013.01)

(58) Field of Classification Search
CPC .. C07C 2/52; C07C 2/86; C07C 15/04; C07C 15/076; C07C 4/18; B01D 3/40
See application file for complete search history.

(56) References Cited

U.S. PATENT DOCUMENTS

| | | |
|---|---|---|
| 6,369,287 B1 | 4/2002 | Magne-Drisch et al. |
| 7,553,998 B2* | 6/2009 | Bresler ................. C07C 5/2708 585/319 |
| 8,889,937 B2* | 11/2014 | Haizmann ............ C10G 29/205 585/323 |
| 9,221,729 B1 | 12/2015 | Lee |
| 10,023,509 B2* | 7/2018 | Pednekar ................. B01D 3/40 |
| 2005/0038308 A1 | 2/2005 | Wolff et al. |
| 2008/0262282 A1* | 10/2008 | Leflaive ................ C07C 5/2737 585/745 |
| 2013/0144097 A1* | 6/2013 | Bender ................... C07C 6/123 585/254 |

OTHER PUBLICATIONS

International Search Report from corresponding PCT Application No. PCT/US2017/023393, dated Jun. 29, 2017.
Extended European Search Report from corresponding European application No. 17776315.8, dated Jan. 17, 2020.

* cited by examiner

PROCESSES AND APPARATUSES FOR NAPHTHENE RECYCLE IN THE PRODUCTION OF AROMATIC PRODUCTS

CROSS-REFERENCE TO RELATED APPLICATIONS

This application is a Continuation of copending International Application No. PCT/US2017/023393 filed Mar. 21, 2017, which application claims priority from U.S. Provisional Application No. 62/316,446 filed Mar. 31, 2016, the contents of which cited applications are hereby incorporated by reference in their entirety.

TECHNICAL FIELD

The technical field generally relates to apparatuses and processes for producing a $C_8$ aromatic isomer product in an aromatics complex. More particularly, the technical field relates to apparatuses and processes for producing para-xylene in an aromatic complex with an integrated scheme for handling naphthenes produced in the process.

BACKGROUND

Most new aromatics complexes are designed to maximize the yield of benzene and $C_8$ aromatic isomer (para-xylene, meta-xylene, ethylbenzene and ortho-xylene). Benzene is a versatile petrochemical building block used in many different products based on its derivation including ethylbenzene, cumene, and cyclohexane. In many instances, the sought $C_8$ aromatic isomer is para-xylene as para-xylene is an important building block, which is used almost exclusively for the production of polyester fibers, resins, and films formed via terephthalic acid or dimethyl terephthalate intermediates. Accordingly, an aromatics complex may be configured in many different ways depending on the desired products, available feedstocks, and investment capital available. A wide range of options permits flexibility in varying the product slate balance of benzene and para-xylene to meet downstream processing requirements.

A prior art aromatics complex flow scheme has been disclosed by Meyers in the HANDBOOK OF PETROLEUM REFINING PROCESSES, 2d. Edition in 1997 by McGraw-Hill.

In an aromatics complex, the production of commercial-grade $C_8$ aromatic isomers involves multiple separation steps such as fractionation, adsorptive separation and/or crystallization and reaction steps including transalkylation, isomerization, dealkylation etc. In typical aromatic complexes used to produce high purity $C_8$ aromatic isomers, the isomer-depleted raffinate stream from the separation process, either simulated moving bed adsorption or crystallization, is sent to an isomerization process in which the remaining xylene isomers are isomerized to produce the desired isomer (near equilibrium concentration) and convert ethylbenzene (EB) to other components which can be separated via fractionation or other means. One type of xylene isomerization process also isomerizes EB to xylenes via a $C_8$ naphthene intermediate. In a typical paraxylene complex using simulated moving bed (SMB) adsorption, the $C_8$ naphthenes remain in the feed to the SMB unit. This is feasible due to the typical use of para-diethylbenzene as the desorbent in the SMB process. In paraxylene complexes using toluene as the SMB desorbent, the majority of the $C_8$ napthenes must be removed from the feed to the SMB unit in order to avoid accumulation of the $C_8$ naphthenes in the circulating toluene desorbent. This also holds true for complexes designed to produce meta-xylene which also utilizes toluene as the SMB desorbent. This is necessary because the $C_8$ naphthene isomers have boiling points within the range of toluene (at the low end) and xylenes (at the high end). As a result, $C_8$ isomers, such as 1,1,3-trimethyl cyclopentane which has a boiling point slightly lower than toluene, will accumulate in the toluene desorbent supply, thus making the material less suitable as a desorbent. In addition, because some of the $C_8$ naphthene isomers have boiling points close to toluene and toluene is a byproduct produced in the xylene/EB isomerization process, it is also necessary to remove toluene from the $C_8$ naphthene recycle stream to avoid accumulation of toluene in the isomerization feed.

Further, in para-xylene complexes which utilize para-diethylbenzene as the SMB desorbent, it may be useful to separate the naphthenes prior to the SMB unit for energy conservation.

Accordingly, it is desirable to provide improved methods and apparatuses for separating $C_8$ naphthenes from an isomerate product stream before being recycled to the xylene separation unit. Further, it is desirable to provide a cost-effective method and apparatus to solve the problem of accumulation of $C_8$ naphthenes in the desorbent supply in a xylene separation unit. Also, it is desirable to remove toluene from the $C_8$ naphthene recycle stream to avoid accumulation of toluene in the isomerization feed. Furthermore, other desirable features and characteristics of the present subject matter will become apparent from the subsequent detailed description of the subject matter and the appended claims, taken in conjunction with the accompanying drawings and this background of the subject matter.

BRIEF SUMMARY

Various embodiments contemplated herein relate to apparatuses and processes for producing a purified $C_8$ aromatic isomer product in an aromatics complex. The exemplary embodiments taught herein include apparatuses and processes producing $C_8$ aromatic isomer product in an aromatic complex with an integrated scheme for handling naphthenes produced in the process.

In accordance with another exemplary embodiment, a process is provided for producing a $C_8$ aromatic isomer product, wherein the process comprises introducing a raffinate product stream comprising $C_8$ aromatic isomers to an isomerization unit to provide an isomerized stream. The isomerized stream is separated to provide a first stream comprising $C_8$ naphthenes and $C_7$ aromatic hydrocarbons and a second stream comprising $C_8$ aromatic isomers. The first stream is passed to an extractive distillation column to provide a recycle feedstream comprising the $C_8$ naphthenes and an extract stream comprising the $C_7$ aromatic hydrocarbons. The recycle feedstream is passed to the isomerization unit.

In accordance with another exemplary embodiment, a process is provided for the production of para-xylene, wherein the process comprises introducing a raffinate product stream comprising $C_8$ aromatic isomers to an isomerization unit to provide an isomerized stream, wherein the isomerized stream is produced in the presence of an ethylbenzene (EB) isomerization catalyst. The isomerized stream is passed to an isomerate stripper column to provide an isomerate stripper overhead stream comprising $C_{6-}$ hydrocarbons and an isomerate stripper bottoms stream. The isomerate stripper bottoms stream is passed to a naphthene splitter column to provide an overhead naphthene splitter stream comprising the $C_8$ naphthenes and $C_7$ aromatic hydrocarbons and a naphthene splitter sidedraw stream comprising $C_8$ aromatic isomers. The overhead naphthene splitter stream is passed to an extractive distillation column to provide a recycle feedstream comprising the $C_8$ naphthenes and an extract stream comprising the $C_7$ aromatic hydrocarbons. The recycle feedstream is passed to the isomerization unit.

In accordance with yet another exemplary embodiment, an apparatus is provided for an apparatus for producing para-xylene, wherein the apparatus comprises an isomerization unit to provide an isomerized stream. An isomerate stripper column is in communication with the isomerization unit to provide an isomerate stripper overhead stream comprising $C_{6-}$ hydrocarbons in an isomerate overhead line and an isomerate stripper bottoms stream in an isomerate bottoms line. A naphthene splitter column is in communication with the isomerate bottoms line to provide an overhead naphthene splitter stream comprising the $C_8$ naphthenes and $C_7$ aromatic hydrocarbons in a naphthene splitter overhead line and a naphthene splitter sidedraw stream comprising $C_8$ aromatic isomers in a naphthene splitter sidedraw line. An extractive distillation column is in communication with the naphthene splitter overhead line to provide a feedstream comprising the $C_8$ naphthenes in a recycle line and an extract stream comprising the $C_7$ aromatic hydrocarbons in an extract line.

These and other features, aspects, and advantages of the present disclosure will become better understood upon consideration of the following detailed description, drawings and appended claims.

BRIEF DESCRIPTION OF THE DRAWINGS

The various embodiments will hereinafter be described in conjunction with the following FIGURES, wherein like numerals denote like elements.

Figure 1:
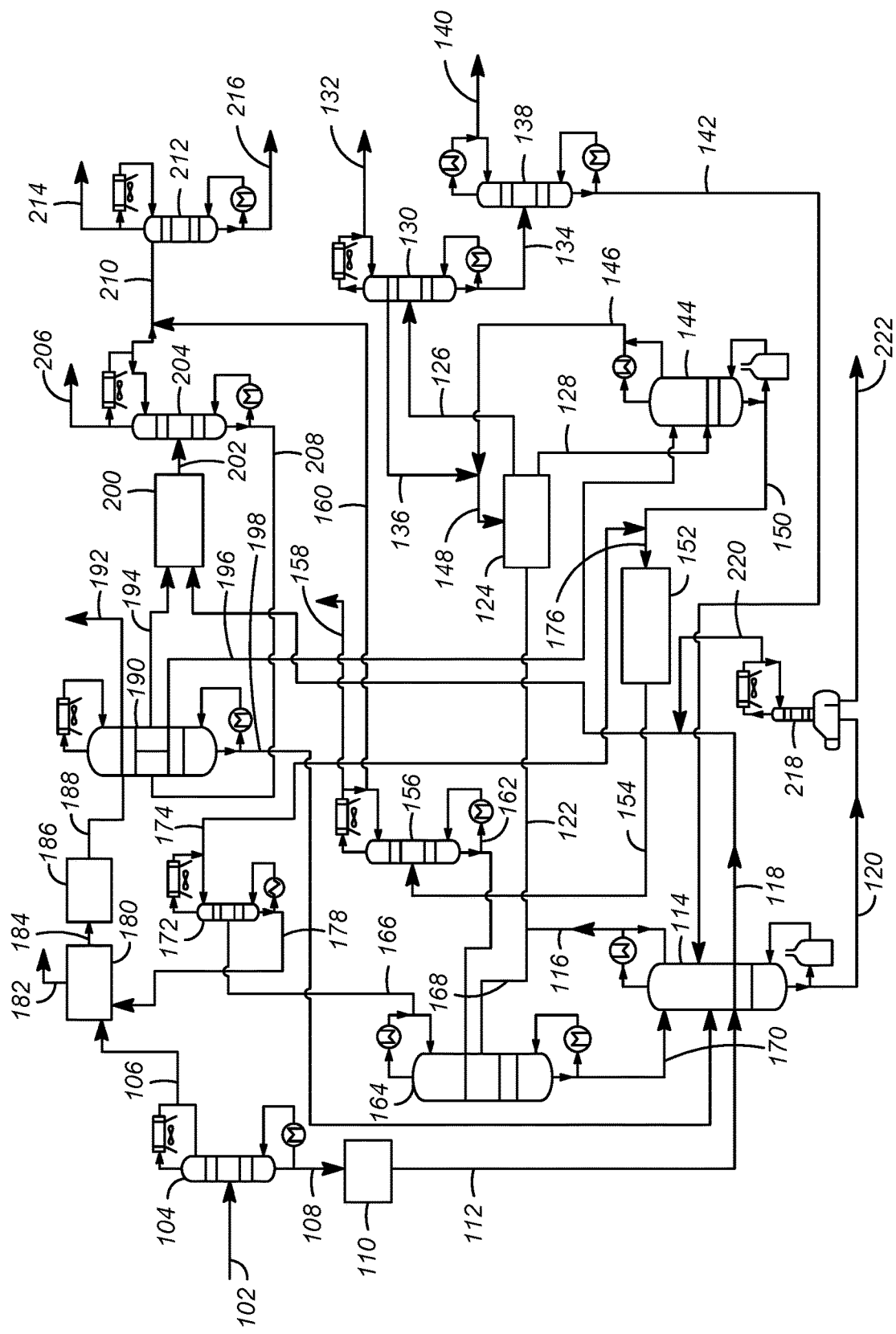
FIG. 1 illustrates an aromatics complex having an integrated scheme for handling naphthenes produced in the process according to an embodiment of the present disclosure.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

DEFINITIONS

As used herein, the term "stream" can include various hydrocarbon molecules and other substances.

As used herein, the term "stream", "feed", "product", "part" or "portion" can include various hydrocarbon molecules, such as straight-chain and branched alkanes, naphthenes, alkenes, alkadienes, and alkynes, and optionally other substances, such as gases, e.g., hydrogen, or impurities, such as heavy metals, and sulfur and nitrogen compounds. Each of the above may also include aromatic and non-aromatic hydrocarbons.

As used herein, the term "overhead stream" can mean a stream withdrawn at or near a top of a vessel, such as a column.

As used herein, the term "bottoms stream" can mean a stream withdrawn at or near a bottom of a vessel, such as a column.

Hydrocarbon molecules may be abbreviated $C_1$, $C_2$, $C_3$, Cn where "n" represents the number of carbon atoms in the one or more hydrocarbon molecules or the abbreviation may be used as an adjective for, e.g., non-aromatics or compounds. Similarly, aromatic compounds may be abbreviated $A_6$, $A_7$, $A_8$, An where "n" represents the number of carbon atoms in the one or more aromatic molecules. Furthermore, a superscript "+" or "−" may be used with an abbreviated one or more hydrocarbons notation, e.g., $C_{3+}$ or $C_{3-}$, which is inclusive of the abbreviated one or more hydrocarbons. As an example, the abbreviation "$C_{3+}$" means one or more hydrocarbon molecules of three or more carbon atoms.

As used herein, the term "zone" or "unit" can refer to an area including one or more equipment items and/or one or more sub-zones. Equipment items can include, but are not limited to, one or more reactors or reactor vessels, separation vessels, distillation towers, heaters, exchangers, pipes, pumps, compressors, and controllers. Additionally, an equipment item, such as a reactor, dryer, or vessel, can further include one or more zones or sub-zones.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top or overhead pressure is the pressure of the overhead vapor at the vapor outlet of the column. The bottom temperature is the liquid bottom outlet temperature. Overhead lines and bottoms lines refer to the net lines from the column downstream of any reflux or reboil to the column unless otherwise shown. Stripping columns omit a reboiler at a bottom of the column and instead provide heating requirements and separation impetus from a fluidized inert media such as steam.

As used herein, the term "rich" can mean an amount of at least generally 50%, and preferably 70%, by mole, of a compound or class of compounds in a stream.

As depicted, process flow lines in the FIGURES can be referred to interchangeably as, e.g., lines, pipes, feeds, gases, products, discharges, parts, portions, or streams.

The term "communication" means that material flow is operatively permitted between enumerated components.

The term "downstream communication" means that at least a portion of material flowing to the subject in downstream communication may operatively flow from the object with which it communicates.

The term "upstream communication" means that at least a portion of the material flowing from the subject in upstream communication may operatively flow to the object with which it communicates.

The term "direct communication" means that flow from the upstream component enters the downstream component without undergoing a compositional change due to physical fractionation or chemical conversion.

The term "predominantly" means a majority, suitably at least 50 mol % and preferably at least 60 mol %.

The term "passing" means that the material passes from a conduit or vessel to an object.

The term "majority" means, suitably at least 40 wt % and preferably at least 50 wt %.

DETAILED DESCRIPTION

The following detailed description is merely exemplary in nature and is not intended to limit the various embodiments or the application and uses thereof. Furthermore, there is no intention to be bound by any theory presented in the preceding background or the following detailed description. Moreover, the reaction conditions including selection of temperature, pressure, LHSV and catalyst in the various units in the aromatics complex described below are conventional which are known to one of ordinary skill in the art, unless wherever mentioned.

Various embodiments are directed to apparatuses and processes for producing a $C_8$ aromatic isomer product in an aromatic complex, wherein the process comprises introducing a raffinate product stream comprising $C_8$ aromatic isomers to an isomerization unit to provide an isomerized stream comprising $C_8$ aromatic isomers, $C_8$ naphthenes and $C_7$ aromatic hydrocarbons in presence of an isomerization catalyst. Isomerization catalysts that can be used in the present disclosure include conventional isomerization catalysts such as those disclosed in U.S. Pat. No. 6,740,788, the teachings of which are incorporated herein by reference. In accordance with an exemplary embodiment, the isomerized stream may be produced in the isomerization unit in the presence of an ethylbenzene (EB) isomerization catalyst. In accordance with an exemplary embodiment, the EB isomerization catalyst may include an MTW type zeolite, an alumina binder and a noble group metal. An exemplary EB isomerization catalyst which may be used in the present disclosure is disclosed in U.S. Pat. No. 7,745,647, the teachings of which are incorporated herein by reference. Subsequently, the isomerized stream is separated to provide a first stream comprising $C_8$ naphthenes and $C_7$ aromatic hydrocarbons and a second stream comprising $C_8$ aromatic isomers. In accordance with various embodiments, the first stream comprises a majority of the $C_8$ naphthenes present in the isomerized stream and the second the stream comprises majority of the $C_8$ aromatic isomers present in the isomerized stream. In accordance with various embodiments, the $C_7$ aromatic hydrocarbon is toluene. The first stream is passed to an extractive distillation column for separation in the presence of a solvent. A recycle feedstream comprising the $C_8$ naphthenes is separated from an extract stream comprising the $C_7$ aromatic hydrocarbons and the solvent in the extractive distillation column. The recycle feedstream may be passed to the isomerization unit. The second stream may be passed to a xylene separation unit to provide a xylene extract stream comprising the $C_8$ aromatic isomer product and the raffinate product stream. The $C_8$ aromatic isomer product that is produced may be one of para-xylene, meta-xylene or ethylbenzene. In accordance with an exemplary embodiment, the xylene separation unit is a para-xylene separation unit. In an aspect, the xylene separation unit may be a simulated moving bed adsorption unit. The xylene separation unit may use a desorbent with a lower boiling point than the $C_8$ aromatic isomers. In an aspect, the desorbent may be toluene.

An exemplary embodiment of the process and apparatus for producing a $C_8$ aromatic isomer product in an aromatic complex is addressed with reference to a process and apparatus 100 illustrating an aromatics complex having an integrated scheme for handling naphthenes produced in the process, according to an embodiment as shown in FIG. 1. The process and apparatus 100 includes a reformate splitter column 104, an aromatics rerun column 114, a xylene separation unit 124, an extract column 130, a xylene column 138, a raffinate column 144, an isomerization unit 152, an isomerate stripper column 156, a naphthene splitter column 164, am extractive distillation column 172, an aromatics extraction unit 180, a benzene-toluene (BT) column 188, a transalkylation unit 200, a transalkylation stripper 204, a stabilizer 212 and a heavy aromatics column 218.

In accordance with an exemplary embodiment as shown in FIG. 1, a reformate stream in line 102 comprising aromatic hydrocarbons may be passed to the reformate splitter column 104. A reformate overhead stream in line 106 comprising $C_{7-}$ aromatic hydrocarbons and a reformate bottoms stream in line 108 comprising $C_{7+}$ aromatic hydrocarbons may be withdrawn from the reformate splitter column 104. In accordance with an instant embodiment as shown, an overhead stream from the reformate splitter column 106 may be condensed and separated in a receiver with a portion of the condensed liquid being refluxed back to the reformate splitter column 104 to obtain the reformate overhead stream from a net portion in line 106. Further, as illustrated, the reformate splitter column 104 may include a reboiler at a bottom of the column to vaporize and send a portion of the reformate bottoms stream back to the bottom of the column. The reformate bottoms stream in line 108 may be passed to the aromatics rerun column 114 for separation. In accordance with an exemplary embodiment as shown in FIG. 1, the reformate bottoms stream in line 108 may be passed through a clay treater 110 to treat residual olefin contaminants and provide a treated reformate bottoms stream in line 112 prior to being passed to the aromatics rerun column 114. The aromatics rerun column 114 may further receive a naphthene splitter bottoms stream in line 170 comprising $C_{8+}$ aromatic hydrocarbons and a benzene toluene (hereinafter "BT") column bottoms stream in line 198 comprising xylenes. Further, the aromatics rerun column 114 may receive $C_{8+}$ aromatic hydrocarbons in a bottoms stream in line 142 from the xylene column 138 discussed later. A net overhead rerun column stream in line 116 comprising $C_8$ aromatic isomers and a net bottoms rerun column stream in line 120 rich in $C_9$ and heavier alkylaromatic hydrocarbons may be withdrawn from the aromatics rerun column 114.

In accordance with an exemplary embodiment as shown, the net overhead rerun column stream may be recovered from an overhead of the aromatics rerun column 114 after condensing, flashing and refluxing a portion of the overhead stream from the column. Further, as illustrated, the aromatics rerun column 114 may include a heater at a bottom of the column to vaporize and send a portion of the bottoms stream back to the bottom of the column. A rerun column sidedraw stream in line 118 rich in $C_9$ and $C_{10}$ alkylaromatics may also be withdrawn from the aromatic rerun column 114. In accordance with an exemplary embodiment as shown in FIG. 1, the rerun column sidedraw stream in line 118 may be passed to the transalkylation unit 200.

In accordance with an exemplary embodiment as shown in FIG. 1, the net overhead rerun column stream in line 116 may be combined with a naphthene splitter sidedraw stream in line 168 comprising $C_8$ aromatic isomers to provide a mixed stream in line 122. The mixed stream in line 122 includes para-xylene, meta-xylene, ortho-xylene and ethylbenzene and may be subsequently passed to the xylene separation unit 124 to obtain a desired $C_8$ aromatic isomer product via a separation process. The xylene separation unit 124 may be one of a para-xylene separation unit, a meta-xylene separation unit or an ortho-xylene separation unit depending on the C8 aromatic product desired and the operating conditions can be tailored accordingly. In accordance with an exemplary embodiment as discussed, the xylene separation unit 124 is a para-xylene separation unit and will be referred to as the para-xylene separation unit 124 for the purpose of the discussion of the instant embodiment. In accordance with the instant embodiment as discussed, the separation process operates, preferably via simulated moving adsorption bed (SMB) employing a desorbent, to provide a xylene extract stream in line 126 which is para-xylene extract stream comprising a mixture of para-xylene and desorbent for the instant embodiment. Examples of desorbent include, and are not limited to toluene and para-diethylbenzene. In accordance with the instant embodiment, toluene is used as the desorbent. The para-xylene extract stream in line 126 may be passed to the extract column 130 which separates para-xylene from the desorbent. A para-xylene stream in line 134 may be withdrawn comprising the desired para-xylenes from the extract column 130. Further, a first return desorbent stream in line 136 is withdrawn which may be subsequently recycled to the para-xylene separation unit 124. In an aspect as shown in FIG. 1, a desorbent drag stream in line 132 may also be withdrawn from the extract column 130. In accordance with an exemplary embodiment, the desorbent drag stream in line 132 may comprise primarily $C_{7-}$ hydrocarbons and may be passed to the BT column 190. In accordance with another exemplary embodiment, the desorbent drag stream in line 132 may be passed to the extractive distillation column 172 to recover additional $C_8$ naphthenes. The para-xylene stream in line 134 may be passed to the para-xylene column to separate the para-xylene product in line 140 from the heavier hydrocarbons obtained as a bottoms stream in line 142 which may be subsequently recycled to the aromatics rerun column 114.

A raffinate stream in line 128 comprising non-equilibrium mixture of $C_8$ aromatics raffinate and the desorbent may be also withdrawn from the para-xylene separation unit 124. The raffinate stream in line 128 may be passed to the raffinate column 144. In accordance with an exemplary embodiment as shown in FIG. 1, a second toluene-enriched stream in line 196 from the BT column 190 may also be introduced to the raffinate column 144 which may act as a makeup for the toluene being used as the desorbent in the para-xylene separation process as per the instant embodiment. The raffinate column 144 separates a raffinate product stream in line 150 for isomerization in isomerization unit 152 from a second return desorbent stream in line 146. In accordance with an exemplary embodiment as shown in FIG. 1, the first desorbent rerun in line 136 and the second desorbent rerun stream in line 146 may combine to provide a combined desorbent rerun stream in line 148 which may be subsequently passed to the para-xylene separation unit 124.

The raffinate product stream in line 150 comprising a non-equilibrium mixture of xylene isomers and ethylbenzene is introduced to the isomerization unit 152 to provide an isomerized stream in line 154. In accordance with an exemplary embodiment as shown in FIG. 1, a recycle feedstream in line 174 (discussed later) from the extractive distillation column 172 may be recycled to the isomerization unit 152. As shown, the recycle stream in line 174 may combine with the raffinate product stream in line 150 to provide a combined stream in line 176 which may be subsequently passed to the isomerization unit 152. The raffinate product stream is isomerized in reactor 152, which contains an isomerization catalyst to provide a product approaching equilibrium concentrations of $C_8$ aromatic isomers. In accordance with the instant embodiment as discussed for producing para-xylenes, additional para-xylene may be produced by reestablishing an equilibrium or near-equilibrium distribution of xylene isomers. Isomerization catalysts that can be used in the present disclosure include conventional isomerization catalysts such as those disclosed in U.S. Pat. No. 6,740,788, the teachings of which are incorporated herein by reference. In accordance with an exemplary embodiment as discussed, the isomerization catalyst is an ethylbenzene (hereinafter "EB") isomerization catalyst. An isomerized stream is withdrawn in line 154 from the isomerization unit 152. In the instant aspect as discussed using an ethylbenzene EB isomerization catalyst, the conversion of ethylbenzene to additional xylenes takes place via a $C_8$ naphthene intermediate. Also, toluene may be produced as a byproduct in the isomerization process. Accordingly, the isomerized stream 154 may include $C_8$ naphthenes and toluene.

The isomerized stream in line 154 may be passed to the isomerate stripper column 156 to separate an isomerate stripper overhead stream comprising $C_{6-}$ hydrocarbons in an isomerate overhead line 160 from an isomerate stripper bottoms stream comprising the C8 naphthenes and toluene in isomerate bottoms line 162, at a first pressure. A vaporous stream in line 158 comprising lighter ends may also be withdrawn from the isomerate stripper column 156 and passed to a vent gas compressor and a stabilizer condenser. The isomerate stripper bottoms stream in isomerate bottoms line 162 may be passed to the naphthene splitter column 164 for further separation. Accordingly, the naphthene splitter column 164 may be in communication with the isomerate bottoms line 162. In an aspect, the naphthene splitter column 164 is in direct, downstream communication with the isomerate bottoms line 162. An overhead naphthene splitter stream in line 166 comprising the $C_8$ naphthenes and toluene is separated from the naphthene splitter bottoms stream in line 170 comprising $C_{8+}$ aromatic hydrocarbons in the naphthene splitter column 164, at a second pressure. In accordance with an exemplary pressure, the second pressure is greater than the first pressure. Accordingly, in an aspect, the naphthene splitter column 164 operates at a higher pressure than the isomerate stripper column 156. Applicants have found that the use of higher pressure in the naphthene splitter column 164 makes the separation more difficult, yet the combination of elevated pressure and narrow boiling range allows the column to be easily heat integrated into the process such that there is no dedicated utility heating or cooling requirements. Further, the naphthene splitter sidedraw stream in line 168 comprising $C_8$ aromatic isomers is also withdrawn which may be subsequently passed to the xylene separation unit 124 for further processing as discussed above. In accordance with various embodiments, the overhead naphthene splitter stream in line 166 comprises a majority of the $C_8$ naphthenes present in the isomerized stream and the naphthene splitter sidedraw stream in line 168 comprises majority of the $C_8$ aromatic isomers present in the isomerized stream.

Subsequently, the overhead naphthene splitter stream in line 166 may be passed to the extractive distillation column 172. Accordingly, the extractive distillation column 172 may be in communication with the naphthene splitter overhead line 166. In an aspect, the extractive distillation column 172 may be in direct, downstream communication with the naphthene splitter overhead line 166. Extractive distillation is a technique for separating mixtures of components having nearly equal volatility and having nearly the same boiling point. In extractive distillation, a solvent is introduced into a main extractive-distillation column above the entry point of the hydrocarbon-containing fluid mixture that is to be separated. The solvent affects the volatility of the hydrocarbon-containing fluid component boiling at a higher temperature differently than the hydrocarbon-containing fluid component boiling at a lower temperature sufficiently to facilitate the separation of the various hydrocarbon-containing fluid components by distillation and such solvent exits with the bottoms fraction. The extractive distillation process in extractive distillation column 172 takes place in the presence of a solvent and separates $C_8$ naphthenes in a recycle feedstream in the recycle line 174 from an extract stream comprising the $C_7$ aromatic hydrocarbons and the solvent withdrawn in an extract line 178. Suitable solvents include tetrahydrothiophene 1, 1-dioxide (or sulfolane), NFM (n-formylmorpholine), NMP (n-methylpyrrolidone), diethylene glycol, triethylene glycol, tetraethylene glycol, methoxy triethylene glycol, and mixtures thereof. Other glycol ethers may also be suitable solvents alone or in combination with those listed above. The recycle feedstream in line 174 may be passed to the isomerization unit 152 and processed together with raffinate product stream in line 150 as discussed above. The extract stream in line 178 may be sent to a solvent-recovery column for the separation of the solvent from the $C_7$ aromatic hydrocarbons. In accordance with an exemplary embodiment as shown in FIG. 1, the extract stream is passed to the aromatics extraction unit 180.

Referring back to the reformate splitter column 104, the reformate overhead stream in line 106 comprising $C_{7-}$ aromatic hydrocarbons may be passed to the aromatics extraction unit 180. The aromatics extraction unit 180 can comprise different methods of separating aromatics from a hydrocarbon stream. One industry standard is the Sulfolane™ process, which is an extractive distillation process utilizing sulfolane to facilitate high purity extraction of aromatics. The Sulfolane™ process is well known to those skilled in the art. An aromatics extract stream in line 184 comprising benzene and toluene and a raffinate stream in line 182 comprising non-aromatic hydrocarbons may be withdrawn from the aromatics extraction unit 180. The aromatics extract stream in line 184 may be passed to the BT column 190 to provide benzene and toluene via separation. In accordance with an exemplary embodiment as shown in FIG. 1, the aromatics extract stream in line 184 may be passed through a clay treater 186 to treat residual olefin contaminants and provide a treated aromatics extract stream in line 188 prior to being passed to the BT column 190. A transalkylation bottom stream in line 208 from the transalkylation stripper column 204 may also be passed to the BT column 190. A benzene-enriched stream in line 192, a first toluene-enriched stream in line 194 and the second toluene-enriched stream in line 196 are withdrawn from the BT column 190. Further, the BT column bottoms stream in line 198 is withdrawn and sent to the aromatics rerun column 114 for further processing as discussed above. The second toluene-enriched stream in line 196 may be passed to the raffinate column 144 as also discussed above. The first toluene-enriched stream in line 194 may be passed to the transalkylation unit 200 for production of additional xylenes and benzene.

In accordance with an exemplary embodiment as shown in FIG. 1, in addition to first toluene-enriched stream, the aromatic rerun column sidedraw stream in line 118 rich in $C_9$ and $C_{10}$ alkylaromatics may be passed to the transalkylation unit 200 along with a heavy aromatics column overhead stream in line 220 rich in $C_9$ and $C_{10}$ alkylaromatics from the heavy aromatics column 218. In accordance with an exemplary embodiment as shown in FIG. 1, the aromatic rerun column sidedraw stream in line 118 and the heavy aromatics column overhead stream in line 220 combine to provide a mixed alkylaromatic feedstream in line 224, which may be subsequently provided to the transalkylation unit 200. A make-up hydrogen gas stream (not shown) may also be provided to the transalkylation unit 200. In the transalkylation unit 200, the incoming feedstreams may be contacted with a transalkylation catalyst under transalkylation conditions. In the transalkylation unit 200, the process continues by transalkylating $C_9$ and $C_{10}$ alkylaromatics with toluene. A transalkylated stream in line 202 comprising benzene and xylenes may be withdrawn from the transalkylation unit 200.

Transalkylation catalysts that can be used in the present disclosure include conventional transkylation catalysts such as those disclosed in U.S. Pat. No. 6,740,788, the teachings of which are incorporated herein by reference. Conditions employed in the transalkylation unit 200 normally include a temperature of from about 200° C. to about 540° C. The transalkylation unit 200 is operated at moderately elevated pressures broadly ranging from about 1 kg/cm' to about 60 kg/cm². The transalkylation reaction can be effected over a wide range of space velocities, with higher space velocities affecting a higher ratio of para-xylene at the expense of conversion. Liquid hourly space velocity generally is in the range of from about 0.1 to about 20 $hr^{-1}$.

The transalkylated stream in line 202 may be sent to transalkylation stripper 204 to recover the transalkylation stripper bottoms stream in line 208. Light ends may be removed in transalkylation stripper overhead stream in line 206 and a net overhead stream in line 210 comprising $C_6$ and lighter hydrocarbons may also be withdrawn from the transalkylation stripper 204. Subsequently, the transalkylation stripper bottoms stream in line 208 may be recycled to the BT column 190 to recover benzene product and unconverted toluene for further processing as previously described. The net overhead stream in line 210 may be passed to the stabilizer 212 to provide a stabilizer overhead vaporous stream in line 214 and a stabilizer bottoms stream in line 216. The stabilizer bottoms stream in line 216 may be passed to the aromatics extraction unit 180.

Referring back to the aromatic rerun column 114, net bottoms rerun column stream in line 120 rich in $C_9$ and heavier alkylaromatic hydrocarbons is passed to the heavy aromatics column 218 to separate heavy aromatics comprising $C_{11+}$ alkylaromatic hydrocarbons from $C_9$ and $C_{10}$ alkylaromatics recovered as the heavy aromatics column overhead stream in line 220. The $C_{11+}$ alkylaromatic hydrocarbons may be withdrawn from the heavy aromatics column 218 as a bottoms stream in line 222. The heavy aromatics column overhead stream in line 220 rich in $C_9$ and $C_{10}$ alkylaromatics may be passed to the transalkylation unit 200 for production of additional xylenes and benzene as previously described.

Figure 2:
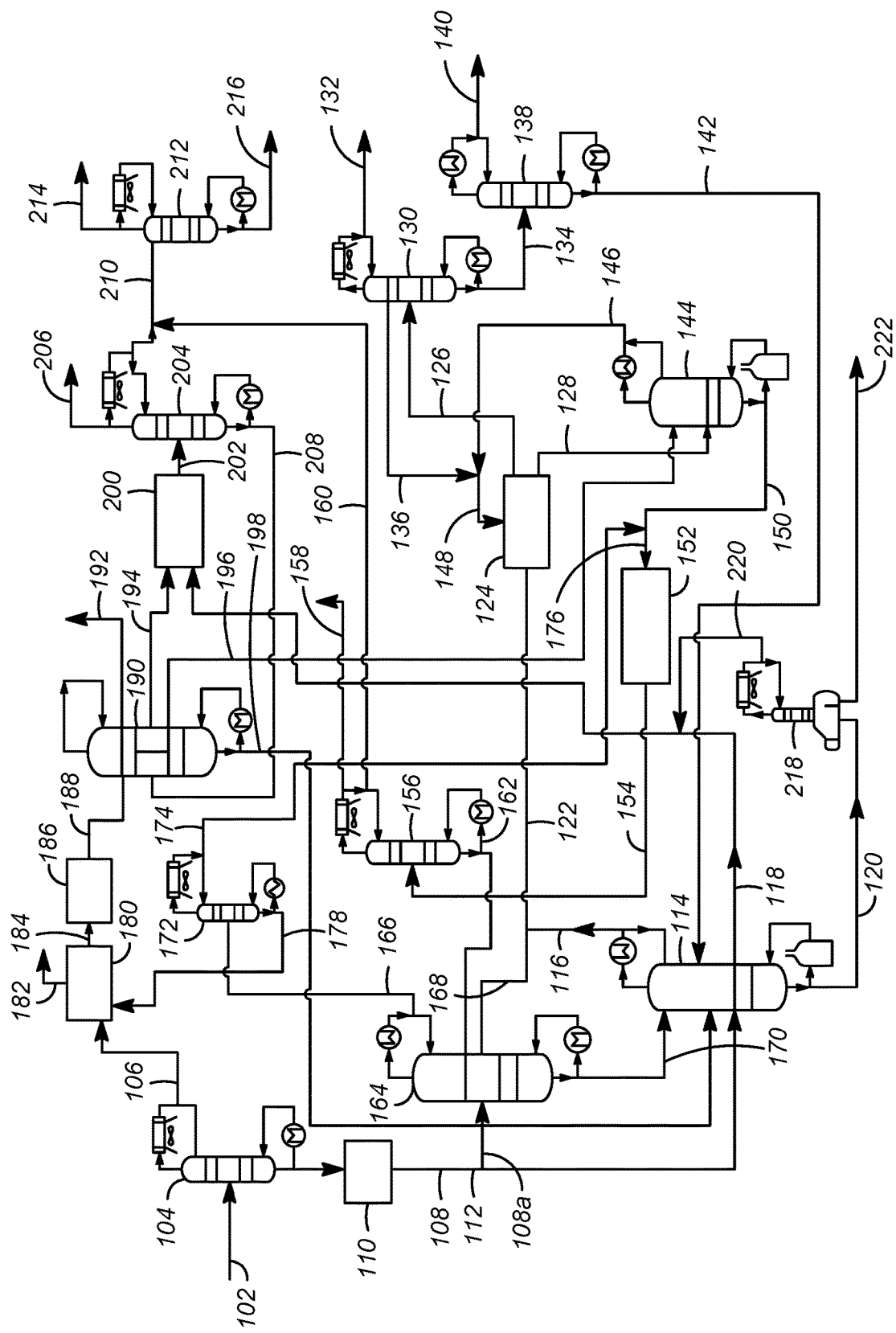
FIG. 2 illustrates an aromatics complex having an integrated scheme for handling naphthenes produced in the process according to another embodiment of the present disclosure.

Turning now to FIG. 2, another embodiment of the aromatics complex is addressed with reference to a process and apparatus 200 providing an alternative integrated scheme for handling naphthenes produced in the process. Many of the elements in FIG. 2 have the same configuration as in FIG. 1 and bear the same respective reference number and have similar operating conditions. Further, the temperature, pressure and composition of various streams are similar to the corresponding streams in FIG. 1, unless specified otherwise. The apparatus and process in FIG. 2 are the same as in FIG. 1 with the exception of the noted following differences. In accordance with the exemplary embodiment as shown in the FIG. 2, a portion of the reformate splitter bottoms stream comprising toluene and $C_{8+}$ aromatic hydrocarbons is withdrawn in line 108a and may be passed to the naphthene splitter column 164 for co-processing with the isomerate bottoms line 162. Accordingly, the naphthene splitter column 164 may be in communication with the reformate bottoms line 108 to receive at least a portion of the reformate bottoms stream. In an aspect, the naphthene splitter column 164 may be in direct, downstream communication with the reformate splitter column 104 via at least a portion of the reformate bottoms stream in line 108a. Streams in line 166, 168 and 170 are withdrawn from the naphthene splitter column 164 which are processed further as described with respect to FIG. 1.

Applicants discovered that by sending a portion of the reformate splitter bottoms stream to the naphthene splitter column as explained with respect to FIG. 2 increases the aromatic content of the feed i.e. overhead naphthene splitter stream in line 166 to the extractive distillation column. The reformate splitter bottoms stream will comprise toluene that will co-boil with the $C_8N$. The toluene will increase the aromatic content of the feed to the extractive distillation column 172 and allow better utilization of the solvent. Concurrently, the aromatics extraction unit will now process less aromatics, effectively shifting the recovery of toluene to the extractive distillation column.

SPECIFIC EMBODIMENTS

While the following is described in conjunction with specific embodiments, it will be understood that this description is intended to illustrate and not limit the scope of the preceding description and the appended claims.

A first embodiment of the invention is a process for producing a $C_8$ aromatic isomer product, wherein the process comprises a) introducing a raffinate product stream comprising $C_8$ aromatic isomers to an isomerization unit to provide an isomerized stream; b) separating the isomerized stream to provide a first stream comprising $C_8$ naphthenes and $C_7$ aromatic hydrocarbons and a second stream comprising $C_8$ aromatic isomers; c) passing the first stream to an extractive distillation column to provide a recycle feedstream comprising the $C_8$ naphthenes and an extract stream comprising the $C_7$ aromatic hydrocarbons; and d) passing the recycle feedstream to the isomerization unit. An embodiment of the invention is one, any or all of prior embodiments in this paragraph up through the first embodiment in this paragraph, wherein the $C_8$ aromatic isomer product is one of a para-xylene, meta-xylene and ethylbenzene. An embodiment of the invention is one, any or all of prior embodiments in this paragraph up through the first embodiment in this paragraph further comprising passing the second stream to a xylene separation unit to provide a xylene extract stream comprising the $C_8$ aromatic isomer product and the raffinate product stream. An embodiment of the invention is one, any or all of prior embodiments in this paragraph up through the first embodiment in this paragraph, wherein the xylene separation unit is a simulated moving bed adsorption unit. An embodiment of the invention is one, any or all of prior embodiments in this paragraph up through the first embodiment in this paragraph, wherein the xylene separation unit uses a desorbent with a lower boiling point than the $C_8$ aromatic isomers. An embodiment of the invention is one, any or all of prior embodiments in this paragraph up through the first embodiment in this paragraph, wherein the desorbent is toluene. An embodiment of the invention is one, any or all of prior embodiments in this paragraph up through the first embodiment in this paragraph, wherein separating the isomerized stream comprises a) passing the isomerized stream to an isomerate stripper column to provide an isomerate stripper overhead stream comprising $C_{6-}$ hydrocarbons and an isomerate stripper bottoms stream; and b) passing the isomerate stripper bottoms stream to a naphthene splitter column to provide the first stream comprising the $C_8$ naphthenes and $C_7$ aromatic hydrocarbons and the second stream comprising $C_8$ aromatic isomers. An embodiment of the invention is one, any or all of prior embodiments in this paragraph up through the first embodiment in this paragraph, wherein the isomerized stream is produced in the presence of an ethylbenzene (EB) isomerization catalyst.

A second embodiment of the invention is a process for the production of para-xylene, wherein the process comprises a) introducing a raffinate product stream comprising $C_8$ aromatic isomers to an isomerization unit to provide an isomerized stream, wherein the isomerized stream is produced in the presence of an ethylbenzene (EB) isomerization catalyst; b) passing the isomerized stream to an isomerate stripper column to provide an isomerate stripper overhead stream comprising $C_{6-}$ hydrocarbons and an isomerate stripper bottoms stream; c) passing the isomerate stripper bottoms stream to a naphthene splitter column to provide an overhead naphthene splitter stream comprising the $C_8$ naphthenes and $C_7$ aromatic hydrocarbons and a naphthene splitter sidedraw stream comprising $C_8$ aromatic isomers; d) passing the overhead naphthene splitter stream to an extractive distillation column to provide a recycle feedstream comprising the $C_8$ naphthenes and an extract stream comprising the $C_7$ aromatic hydrocarbons; and e) passing the recycle feedstream to the isomerization unit. An embodiment of the invention is one, any or all of prior embodiments in this paragraph up through the second embodiment in this paragraph further comprising providing a reformate stream comprising aromatic hydrocarbons to a reformate splitter to provide a reformate bottoms stream comprising $C_{7+}$ aromatic hydrocarbons and a reformate overhead stream comprising $C_{7-}$ aromatic hydrocarbons. An embodiment of the invention is one, any or all of prior embodiments in this paragraph up through the second embodiment in this paragraph further comprising passing a portion of the reformate bottoms stream from the reformate splitter to the naphthene splitter column. An embodiment of the invention is one, any or all of prior embodiments in this paragraph up through the second embodiment in this paragraph further comprising passing the naphthene splitter sidedraw stream to a para-xylene separation unit to provide a xylene extract stream comprising para-xylene and the raffinate product stream and passing a naphthene splitter bottoms stream comprising $C_{8+}$ aromatic hydrocarbons to an aromatics rerun column. An embodiment of the invention is one, any or all of prior embodiments in this paragraph up through the second embodiment in this paragraph wherein the para-xylene separation unit is a simulated moving bed adsorption unit. An embodiment of the invention is one, any or all of prior embodiments in this paragraph up through the second embodiment in this paragraph, wherein the para-xylene separation unit uses a desorbent with a lower boiling point than the $C_8$ aromatic isomers. An embodiment of the invention is one, any or all of prior embodiments in this paragraph up through the second embodiment in this paragraph, wherein the desorbent is toluene. An embodiment of the invention is one, any or all of prior embodiments in this paragraph up through the second embodiment in this paragraph, wherein the isomerate stripper column and the naphthene splitter column operate at a first pressure and a second pressure respectively, wherein the second pressure is greater than the first pressure.

A third embodiment of the invention is an apparatus for producing para-xylene, wherein the apparatus comprises a) an isomerization unit to provide an isomerized stream; b) an isomerate stripper column in communication with the isomerization unit to provide an isomerate stripper overhead stream comprising $C_{6-}$ hydrocarbons in an isomerate overhead line and an isomerate stripper bottoms stream in an isomerate bottoms line; c) a naphthene splitter column in communication with the isomerate bottoms line to provide an overhead naphthene splitter stream comprising the $C_8$ naphthenes and $C_7$ aromatic hydrocarbons in a naphthene splitter overhead line and a naphthene splitter sidedraw stream comprising $C_8$ aromatic isomers in a naphthene splitter sidedraw line; and d) an extractive distillation column in communication with the naphthene splitter overhead line to provide a recycle feedstream comprising the $C_8$ naphthenes in a recycle line and an extract stream comprising the $C_7$ aromatic hydrocarbons in an extract line. An embodiment of the invention is one, any or all of prior embodiments in this paragraph up through the third embodiment in this paragraph further comprising a reformate splitter providing a reformate bottoms stream comprising $C_{7+}$ aromatic hydrocarbons in a reformate bottoms line and a reformate overhead stream comprising $C_{7-}$ aromatic hydrocarbons in a reformate overhead line. An embodiment of the invention is one, any or all of prior embodiments in this paragraph up through the third embodiment in this paragraph, wherein the naphthene splitter column is in communication with the reformate bottoms line to receive at least a portion of the reformate bottoms stream. An embodiment of the invention is one, any or all of prior embodiments in this paragraph up through the third embodiment in this paragraph further comprising a para-xylene separation unit in communication with the naphthene splitter sidedraw line, the para-xylene separation unit being a simulated moving bed adsorption unit using toluene as a desorbent.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for producing a $C_8$ aromatic isomer product, wherein the process comprises:
   a) introducing a raffinate product stream comprising $C_8$ aromatic isomers to an isomerization unit to provide an isomerized stream;
   b) separating the isomerized stream in a separation zone comprising a isomerate stripper column and a naphthene splitter column to provide a first stream comprising $C_8$ naphthenes and $C_7$ aromatic hydrocarbons and a second stream comprising $C_8$ aromatic isomers;
   c) passing the first stream to an extractive distillation column to provide a recycle feedstream comprising the $C_8$ naphthenes and an extract stream comprising the $C_7$ aromatic hydrocarbons;
   d) passing the recycle feedstream to the isomerization unit;
   e) providing a reformate stream comprising aromatic hydrocarbons to a reformate splitter to provide a reformate bottoms stream comprising $C_{7+}$ aromatic hydrocarbons and a reformate overhead stream comprising $C_{7-}$ aromatic hydrocarbons; and
   f) passing a portion of the reformate bottoms stream from the reformate splitter to the naphthene splitter column.

2. The process of claim 1, wherein the $C_8$ aromatic isomers are one of a paraxylene, meta-xylene and ethylbenzene.

3. The process of claim 1 further comprising passing the second stream to a xylene separation unit to provide a xylene extract stream comprising the $C_8$ aromatic isomer product and the raffinate product stream.

4. The process of claim 3, wherein the xylene separation unit is a simulated moving bed adsorption unit.

5. The process of claim 4, wherein the xylene separation unit uses a desorbent with a lower boiling point than the $C_8$ aromatic isomers.

6. The process of claim 5, wherein the desorbent is toluene.

7. The process of claim 1, wherein separating the isomerized stream comprises:
   a) passing the isomerized stream to the isomerate stripper column to provide an isomerate stripper overhead stream comprising C6- hydrocarbons and an isomerate stripper bottoms stream; and
   b) passing the isomerate stripper bottoms stream to the naphthene splitter column to provide the first stream comprising the $C_8$ naphthenes and $C_7$ aromatic hydrocarbons and the second stream comprising $C_8$ aromatic isomers.

8. The process of claim 1, wherein the isomerized stream is produced in the presence of an ethylbenzene (EB) isomerization catalyst.

9. A process for the production of para-xylene, wherein the process comprises:
   a) introducing a raffinate product stream comprising $C_8$ aromatic isomers to an isomerization unit to provide an isomerized stream, wherein the isomerized stream is produced in the presence of an ethylbenzene (EB) isomerization catalyst;
   b) passing the isomerized stream to an isomerate stripper column to provide an isomerate stripper overhead stream comprising $C_{6-}$ hydrocarbons and an isomerate stripper bottoms stream;
   c) passing the isomerate stripper bottoms stream to a naphthene splitter column to provide an overhead naphthene splitter stream comprising the $C_8$ naphthenes and $C_7$ aromatic hydrocarbons and a naphthene splitter sidedraw stream comprising $C_8$ aromatic isomers;
   d) passing the overhead naphthene splitter stream to an extractive distillation column to provide a recycle feedstream comprising the $C_8$ naphthenes and an extract stream comprising the $C_7$ aromatic hydrocarbons;
   e) passing the recycle feedstream to the isomerization unit;
   f) providing a reformate stream comprising aromatic hydrocarbons to a reformate splitter to provide a reformate bottoms stream comprising $C_{7+}$ aromatic hydrocarbons and a reformate overhead stream comprising $C_{7-}$ aromatic hydrocarbons; and g) passing a portion of the reformate bottoms stream from the reformate splitter to the naphthene splitter column.

10. The process of claim 9 further comprising passing the naphthene splitter sidedraw stream to a para-xylene separation unit to provide a xylene extract stream comprising paraxylene and the raffinate product stream and passing a naphthene splitter bottoms stream comprising $C_{8+}$ aromatic hydrocarbons to an aromatics rerun column.

11. The process of claim 10 wherein the para-xylene separation unit is a simulated moving bed adsorption unit.

12. The process of claim 11, wherein the para-xylene separation unit uses a desorbent with a lower boiling point than the $C_8$ aromatic isomers.

13. The process of claim 12, wherein the desorbent is toluene.

14. The process of claim 9, wherein the isomerate stripper column and the naphthene splitter column operate at a first pressure and a second pressure respectively, wherein the second pressure is greater than the first pressure.

\* \* \* \* \*